US00PP35534P2

(12) United States Plant Patent
Bergman

(10) Patent No.: US PP35,534 P2
(45) Date of Patent: Dec. 12, 2023

(54) ***LANTANA* PLANT NAMED 'LANZ0044'**

(50) Latin Name: ***Lantana camara* L.**
Varietal Denomination: LANZ0044

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/803,479

(22) Filed: Jul. 28, 2022

(51) Int. Cl.
*A01H 5/00* (2018.01)
*A01H 6/86* (2018.01)

(52) U.S. Cl.
USPC ..... Plt./227

(58) Field of Classification Search
USPC ..... Plt./226, 227
See application file for complete search history.

(56) References Cited

PUBLICATIONS

CPVO Register. Citation for 'LANZ0044'. https://online.plantvarieties.eu/publicSearch?order=denomination&denomination=LANZ0044 (Year: 2023).*

* cited by examiner

*Primary Examiner* — Karen M Redden
(74) *Attorney, Agent, or Firm* — Dale Skalla

(57) ABSTRACT

A new *Lantana* plant named 'LANZ0044' having medium size mature cherry pink flowers with pale yellowish-pink immature flowers in the center of the umbel, excellent flower production, vigorous plant growth and uniform dense rounded habit with medium sized dark green foliage.

1 Drawing Sheet

Figure 1:
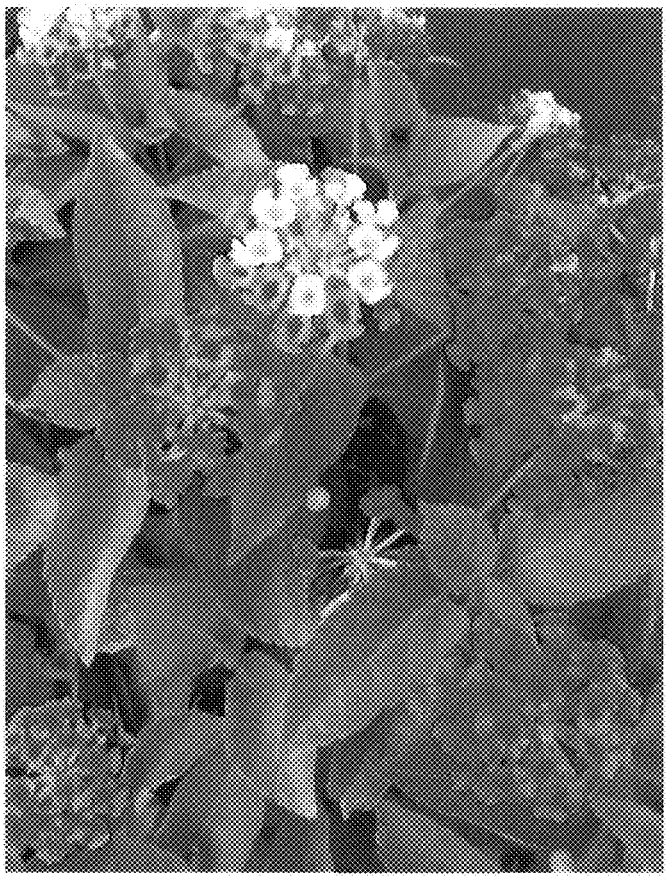

Latin name of the genus and species of the plant claimed: *Lantana camara* L.

Varietal denomination: 'LANZ0044'.

BACKGROUND OF THE NEW PLANT

The present invention comprises a new *Lantana*, botanically known as *Lantana camara* L., and hereinafter referred to by the variety name 'LANZ0044'.

'LANZ0044' is a product of a planned breeding program in Gilroy, California. The new cultivar 'LANZ0044' exhibits medium size mature cherry pink flowers with pale yellowish-pink immature flowers in the center of the umbel, excellent flower production, vigorous plant growth and uniform dense rounded habit with medium sized dark green foliage.

The new *Lantana* cultivar, 'LANZ0044', is the result of an open hybridization in an outdoor field in made in Gilroy, California in the summer of 2016. The female parent of the new cultivar is the commercially available *Lantana camara* variety 'Little Lucky Hot Pink', characterized by its dark cherry red inflorescences, medium green-colored foliage and vigorous spreading growth habit. 'LANZ0044' differs from 'Little Lucky Hot Pink', 'Flortanapi', U.S. Plant Pat. No. 24,555, by having lighter flower color, more uniform and rounded plant habit, and greater flower coverage. The male parent of the new cultivar is not known.

The seed was sown in August 2017 in a controlled greenhouse environment in Gilroy, California, and 'LANZ0044' was selected as one flowering plant within the progeny of the stated cross in November 2017.

The first act of asexual reproduction of 'LANZ0044' was accomplished when vegetative cuttings were propagated from the initial selection February 2018, in Gilroy, California.

BRIEF SUMMARY OF INVENTION

Horticultural examination of plants grown from cuttings of the plant initiated in February 2018, in Gilroy, California, and continuing thereafter, has, demonstrated that the combination of characteristics as herein disclosed for 'LANZ0044' are firmly fixed and are retained through successive generations of asexual reproduction.

'LANZ0044' has not been observed under all possible environmental conditions. The phenotype may vary significantly with variations in environment such as temperature, light intensity, and day length.

Plant Breeder's Rights for this cultivar were applied for in the European Union on Jul. 21, 2022, No. 2022/1755 and in Canada on Sep. 28, 2022, No. 22-11083 'LANZ0044' has not been made publicly available prior to the effective filing date of this application, notwithstanding any disclosure that may have been made less than one year prior to the effective filing date of this application by the inventor or another who obtained 'LANZ0044' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0044' with colors being as true as possible with an illustration of this type.

Figure 2:
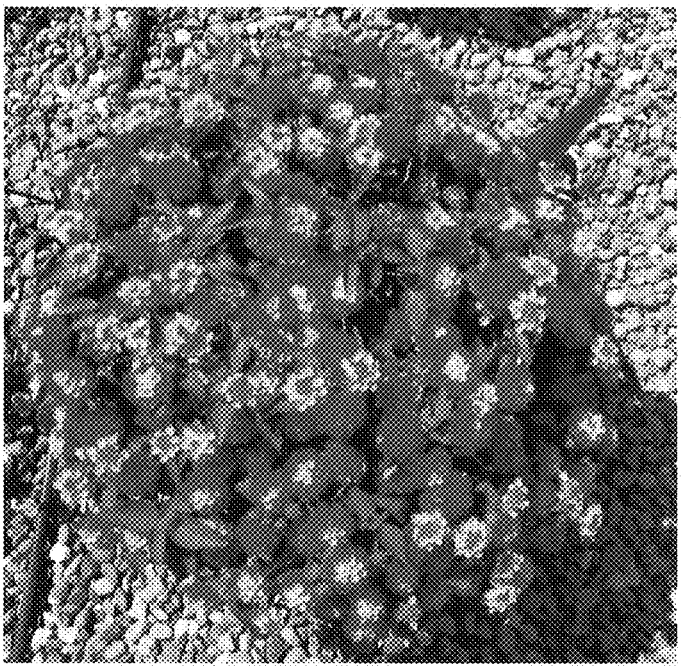

The photographic drawings show in FIG. 1 a close view of an inflorescence taken in September 2021, and in FIG. 2 a whole flowering plant taken in July 2021.

DETAILED BOTANICAL DESCRIPTION

The plant descriptions and measurements were taken in Gilroy, California June 2022. The plants were approximately 3 months old and were growing in 14 inch pots, three plants per pot, in an outdoor field.

Color references are made to The Royal Horticultural Society Colour Chart (RHS) 2001.

TABLE 1

DIFFERENCES BETWEEN THE NEW VARIETY 'LANZ0044' AND A MOST SIMILAR VARIETY

| | 'LANZ0044' | 'Bante Cheria' (U.S. Plant Pat. No. 18,115) |
|---|---|---|
| Plant habit: | 20% Larger plant size | 20% Smaller plant size |
| Flower color: | Pale yellow to pink to dark rose pink | Yellow to dark coral to dark cherry pink |
| Seed set: | Low seed set | Heavy seed set |

The comparison was made of plants grown side by side at the same time, the same way out of doors where pollinators of bees, hummingbirds, butterflies and moths were constantly visiting. The patent for 'Bante Cheria' states the plants were approximately 9-11 week old plants, grown in a greenhouse in Hillscheid, Germany in the summer of 2005. There would not have been the visiting pollinators in this case to result in the heavy seed set seen on this variety when grown out of doors in California.

Plant:

*Form, growth and habit.*—Semi-woody, grown as an annual or perennial; vigorous semi-upright habit; very well branched.
*Plant height.*—16 cm.
*Plant height (inflorescence included).*—20 cm.
*Plant width.*—32 cm.

Foliage:

*Type.*—Opposite.
*Immature, leaf color, upper surface.*—Closest to RHS137A.
*Lower surface.*—Closest to RHS 137C.
*Mature, leaf color, upper surface.*—RHS 139A.
*Lower surface.*—Closest to RHS 137B.
*Length.*—5.2-6.0 cm.
*Width.*—4.3-4.6 cm.
*Shape.*—Ovate.
*Base shape.*—Rounded to truncate.
*Apex shape.*—Acute.
*Margin.*—Serrate.
*Texture, upper.*—Hairy.
*Texture, lower surface.*—Hairy.
*Pattern of veining.*—Pinnate.
*Petiole color.*—RHS 138B.
*Petiole length.*—1.6-2.6 cm.
*Diameter of petiole.*—02.0 cm.
*Texture (upper and lower surface).*—Very short hairs.

Stem:

*Color of stem.*—RHS 138B.
*Length of stem.*—12.0-14.5 cm.
*Diameter.*—0.3 cm.
*Length of internodes.*—2.8-4.0 cm.
*Texture.*—Some hairs.

Inflorescence:

*Type.*—Umbel like, flattened semi-sphere the florets are sessile on an ovate receptacle.
*Blooming habit.*—Flowers continuously from spring through fall.
*Number of open flowers per inflorescence.*—About 37.
*Quantity of inflorescences per plant.*—About 12.
*Lastingness of individual blooms on the plant.*—About 3 weeks (depending on temperatures).
*Fragrance.*—Slightly spicy.
*Umbel horizontal diameter.*—4.2 cm.
*Umbel vertical height.*—2.4 cm.
*Peduncle color.*—RHS 138B.
*Length of peduncle.*—3.0-4.1 cm.
*Peduncle diameter.*—0.15-0.2 cm.
*Texture.*—Some hairs.

Flower:

*Floret form.*—Corolla salver-shaped to shallow cup-shaped, with a relatively long tube at the base; each flower subtended by a single bract.
*Length of floret.*—1.2 cm.
*Width of floret.*—0.9 cm.
*Depth of floret.*—1.7 cm.
*Young floret, color upper surface.*—RHS 62C and RHS 62D with RHS 12B around throat.
*Young floret, color lower surface.*—RHS 62D with tones of RHS 70B.
*Mid age floret, color upper surface.*—RHS 72C with tones of RHS 80B.
*Mid age floret, color lower surface.*—RHS 78C with tones of RHS 78A.
*Mature florets, color upper surface.*—Closest to RHS 71C and RHS 71B.
*Mature floret, color lower surface.*—Closest to RHS 70A and tones of RHS 70D.
*Apex shape.*—Mucronulate.
*Degree of lobation.*—Moderate.
*Margin.*—Entire.
*Base.*—Fused.
*Texture, upper surface.*—Smooth.
*Lower surface.*—Smooth.
*Tube, color outer surface.*—Closest to RHS 70C and RHS 70D.
*Tube, color inner surface.*—RHS 65D.
*Tube, length.*—1.2 cm.
*Tube, diameter (at opening).*—0.2 cm.
*Tube, texture outer surface.*—Smooth.
*Inner surface.*—Very small hairs.

Bud (just before opening):

*Color.*—RHS 61B.
*Length.*—1.0 cm.
*Width.*—0.3 cm at the apex.
*Shape.*—Tubular with a flared apex.

Bract:

*Color.*—Closest to RHS 139B.
*Length.*—0.7-0.9 cm.
*Diameter.*—0.2 cm.
*Texture, upper surface.*—Small hairs.
*Lower surface.*—Small hairs.

Calyx:

*Number of sepals.*—5, fused sepals forming a short tube around the base of the floret.
*Color of sepals.*—Closest to RHS 138D.

*Length of sepals.*—0.3 cm.
*Width of sepals.*—0.2 cm.
*Apex shape.*—Obtuse.
*Apex margins.*—Entire.
*Texture, outer surface.*—Small hairs.
*Inner surface.*—Smooth.

Reproductive organs:

*Gynoecium.*—
*Pistil quantity.*—One.
*Length.*—0.45 cm.
*Style color.*—RHS 150D.
*Style length.*—0.3 cm.
*Stigma color.*—RHS 144B.
*Ovary color.*—RHS 144B.
*Ovary length.*—0.1 cm.
*Ovary diameter.*—0.1 cm.
*Androecium.*—
*Stamen quantity.*—4.
*Color of filaments.*—RHS 159D.
*Length filaments.*—0.05 cm.
*Anther color.*—RHS 161B.
*Length of anthers.*—0.1 cm.
*Color of pollen.*—Unable to discern.
*Pollen amount.*—Unable to discern.
*Fertility/seed set.*—Low.
*Disease/pest resistance.*—Has not been determined to date.
*Winter hardines.*—USDA zone 10a.
*Heat/drought tolerance.*—Very tolerant.

What is claimed is:

1. A new and distinct variety of *Lantana* plant named 'LANZ0044' substantially as illustrated and described herein.

* * * * *